United States Patent [19]
Laird et al.

[11] 3,930,413
[45] Jan. 6, 1976

[54] QUICK RELEASE GAUGE FITTING

[75] Inventors: Richard P. Laird; William M. Sills, both of Peoria, Ill.

[73] Assignee: Caterpillar Tractor Co., Peoria, Ill.

[22] Filed: Aug. 27, 1973

[21] Appl. No.: 391,859

Related U.S. Application Data

[63] Continuation-in-part of Ser. No. 312,820, Dec. 7, 1972, abandoned.

[52] U.S. Cl............... 73/421 B; 73/420; 73/422 R; 137/317
[51] Int. Cl.²......................................... G01N 1/10
[58] Field of Search............. 73/420, 421 B, 422 R; 137/317, 223; 138/90

[56] References Cited
UNITED STATES PATENTS

| | | | |
|---|---|---|---|
| 2,400,955 | 5/1946 | Samel | 137/223 |
| 2,710,623 | 6/1955 | Kolos | 137/223 |
| 3,238,784 | 3/1966 | Dorsey | 73/425 |
| 3,438,397 | 4/1969 | Gilpin | 137/317 |
| 3,477,438 | 11/1969 | Allen et al. | 137/223 |

*Primary Examiner*—S. Clement Swisher
*Attorney, Agent, or Firm*—Phillips, Moore, Weissenberger Lempio & Strabala

[57] ABSTRACT

A fitting is associated with a closed fluid system for allowing testing by means of a probe, meanwhile insuring the system is maintained in a closed condition. Such fitting has a resilient rubber member one side of which is exposed to the fluid in the system, and the other side of which is exposed to outside the system. The rubber member defines a passage from one side to the other which is held closed by the rubber member mounting means, which compress the rubber member to so close the passage. A testing probe may be pushed into and through this passage, to be exposed to the fluid in the system. The resilient member is in sealing contact with the probe when it is so introduced, and upon removal of the probe, the passage again closes, insuring that the system is continuously in a closed condition.

3 Claims, 4 Drawing Figures

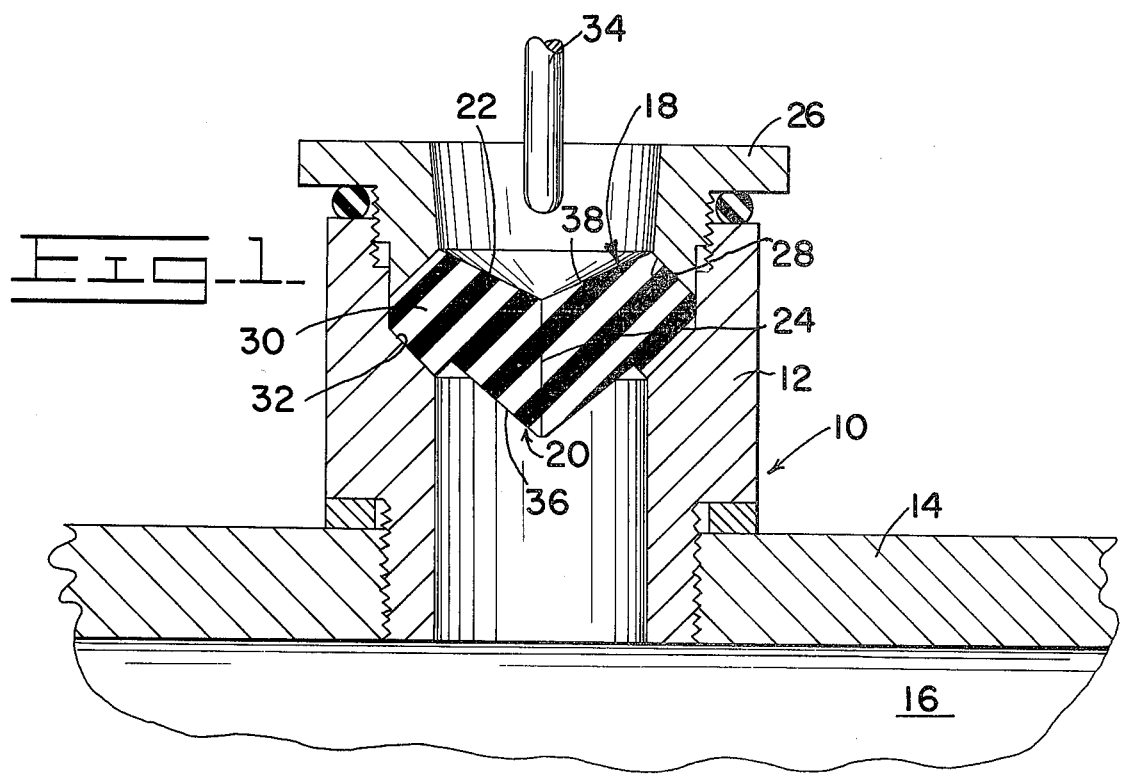
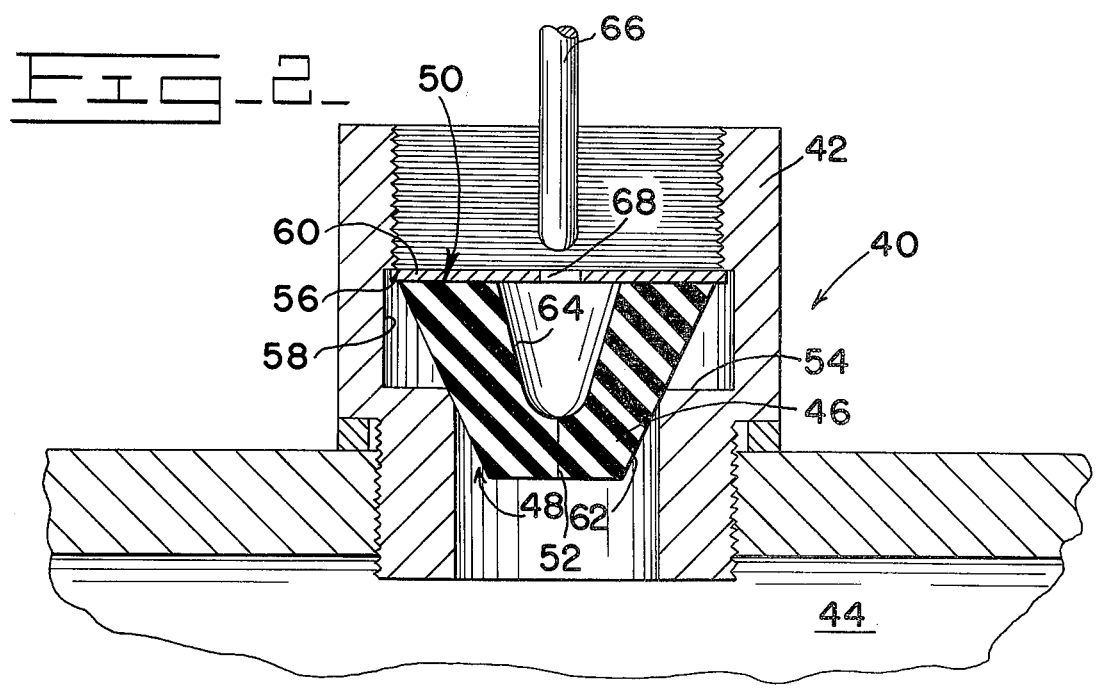

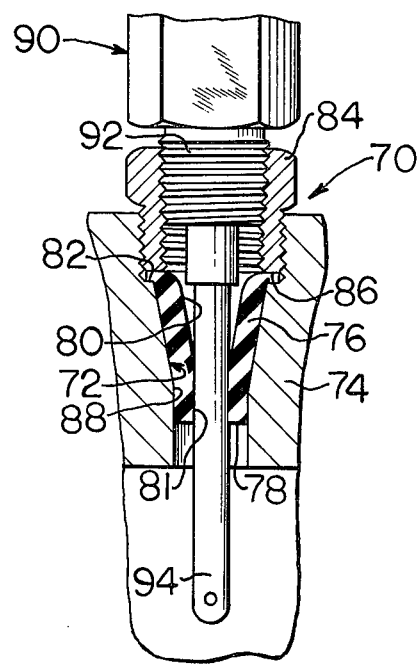
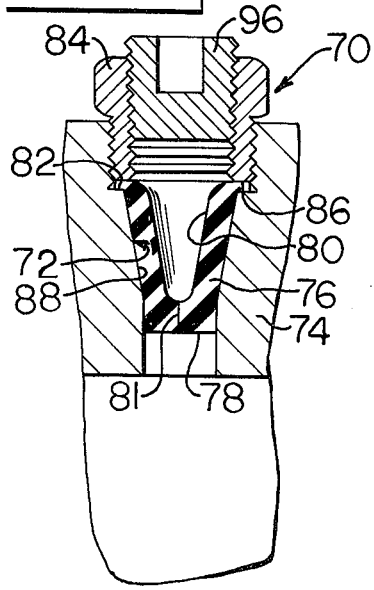

QUICK RELEASE GAUGE FITTING

CROSS REFERENCE TO RELATED APPLICATION

This is a continuation-in-part application of pending application Ser. No. 312,820, filed Dec. 7, 1972 by Richard P. Laird, et al. for "Quick Release Gauge Fitting" now abandoned.

BACKGROUND OF THE INVENTION

This invention relates to sampling of fluid within a closed system, and more particularly, to a fitting of the type which allows sampling of said fluid, meanwhile maintaining the system in its closed condition.

The testing or trouble shooting of a mechanical apparatus such as power plant or engine often involves sampling the temperature and/or pressure of fluids within a closed system of the apparatus. These fluids may take the form of cooling, lubricating, or fuel agents, and variations in their temperature and/or pressure can indicate if the apparatus is functioning properly.

In order to sample a closed system fluid, it is the general practice to attach a fitting or valve of some type to a portion of the system carrying the fluid. Since the fluid will, of necessity, be exposed to the atmosphere for some limited period of time during connection of the fitting, the system or apparatus must be shut down to prevent loss of fluid and/or to prevent a safety hazard to personnel working on the system. Shutdown of the system or apparatus is time-consuming and often requires an additional running time to ring the fluid back to operating temperature or pressure after shutdown.

Additionally, connection of a fitting to the system generally results in some loss of fluid which must be replaced after the connection is completed.

SUMMARY OF THE INVENTION

It is an object of the invention to provide a fitting associated with a closed fluid system which allows testing of the fluid, meanwhile insuring that a closed system is maintained, i.e., no system shutdown is required, and no loss of fluid results.

It is a further object of this invention to provide a fitting which, while fulfilling the above object, is normally connected to the system and need not be removed or replaced for and during the use thereof.

It is a still further object of this invention to provide a fitting which, while fulfilling the above objects, is extremely simple in design and operation.

Broadly stated, the invention comprises apparatus for allowing introduction of a testing probe into a closed fluid system, meanwhile maintaining said system in its closed condition. Such inventive apparatus comprises a resilient member having one side exposed to the fluid within the system, and the other side exposed to outside the system, said resilient member defining a passage from said one side to said other side. Means are included for closing the passage and holding the passage closed to maintain the system in a closed state. The probe means are introducible from the other side of the resilient member into and through the passage, in sealing engagement with the resilient member, opening the passage thereby, and into the fluid system, the removal of the probe means allowing the passage to close, whereby the system is continuously maintained in a closed condition.

BRIEF DESCRIPTION OF THE DRAWINGS

These and other objects of the invention will become apparent from a study of the following specification and drawings, in which:

FIG. 1 is a sectional elevation of a first embodiment of the invention;

FIG. 2 is a sectional elevation of a second embodiment of the invention; and

FIGS. 3 and 4 are sectional elevations of a third embodiment of the invention.

DESCRIPTION OF THE PREFERRED EMBODIMENTS

Shown in FIG. 1 is a first embodiment of fitting 10. The fitting 10 includes a tubular member 12 secured to the body of fluid carrying means 14, which define a fluid carrying chamber 16 as part of a closed fluid system. Such tubular member 12, as shown, communicates with the fluid within the system. A resilient rubber member 18 is disposed within the tubular member 12 and has one side 20 exposed to the fluid within the system and the other side 22 exposed to outside the system. The rubber member 18 defines a central passage 24 which runs from the one side 20 to the other side 22 thereof.

A clamp member 26 is threadably connected with the tubular member 12 and defines an annular surface 28 which is positioned to bear on the side 22 of the rubber member 18 about the edge 30 of the rubber member 18. The tubular member 12 defines an annular step 32 positioned to bear upon the rubber member 18 on the side 20 thereof about the edge 30 of the rubber member 18. Upon tightening of the clamp member 26, it will be seen that rubber member 18 is held within the tubular member 12 in substantially sealing relation therewith.

It will also be seen that the annular surface 28 and the annular step 32 are angled together outwardly of the rubber member 18 and positioned about portions of the resilient member 18, on either side of the edge 30. Such annular surface 28 and annular step 32, upon tightening of the clamp 26 act to compress the resilient member 18 inwardly to close the passage 24 and to hold the passage 24 closed. Closing of said passage 24, it is seen, maintains the fluid system in a closed state.

Sampling of the fluid within the closed fluid system is accomplished by means of a sampling or testing probe 34. To test said fluid, probe 34 is forcibly introduced through the normally closed passage 24 from the side 22 of the rubber member 18 to the side 20 thereof. Said passage 24 is opened thereby, meanwhile with the probe 34 being in sealing engagement with the rubber member 18, keeping the fluid system closed. Said probe 34 thus enters the fluid system, whereby such fluid may be sampled. Any type of instrument or measuring device can be secured to the probe 34 for measuring the characteristics of the fluid within the fluid carrying chamber 16. These instruments can, for example, measure temperature and/or pressure of the fluid. Since the rubber member 18 is under compressive forces, a fluid-type seal is established between the probe 34 and the rubber member 18, therefore, no fluid escapes from the chamber 16 as the probe 34 is inserted through the passage 24.

Removal of the probe 34 allows the passage 24 to close again. Thus, the system is continuously maintained in a closed condition, with no loss of fluid therefrom.

It is to be noted that rubber member 18 defines on the side 20 (which is exposed to the fluid within the system) an annular surface portion 36 which is angled toward the passage 24 and inward of the fluid system. In such case, fluid within the system acts on said surface portion 36 to aid in closing passage 24, to in turn maintain the passage 24 in a closed state.

In addition, rubber member 18 defines on side 22 thereof an annular surface portion 38 which is also angled toward the passage 24 and inward of the fluid system. Such surface portion 38 aids in directing the probe 34 to the passage 24, so that it can be properly inserted therethrough.

Shown in FIG. 2 is a second embodiment of fitting 40. Such fitting is similar to that shown in FIG. 1 and operates in a similar manner. However, some design differences exist, and will now be described.

A tubular member 42 communicates with fluid within a fluid carrying chamber 44, which is part of a closed fluid system. Such tubular member 42 has a rubber member 46 disposed therewithin, with one side 48 exposed to the fluid within the system and the other side 50 exposed to outside the system. A passage 52 runs from side 48 to side 50, as shown.

A shoulder 54 is defined by the tubular member 42 inwardly thereof. With the rubber member 46 in position as shown, the shoulder 54 bears continuously on the side 48 thereof. A shoulder 56 is also defined by the tubular member 42 inwardly thereof, and a recessed portion 58 interconnects the shoulders 54, 56. A washer 60 is inserted to contact shoulder 56, and to bear on the side 50 of the rubber member 46. Through such means, the rubber member 46 is held within the tubular member 42 in continuous substantially sealing relation therewith. In addition, passage 52 is compressed closed by means of shoulder 54, within which a portion of the rubber member 46 is disposed as shown.

Similar to the previous embodiment, rubber member 46 defines an annular surface portion 62 on the side 48 thereof which is exposed to the fluid within the system, and which is angled toward the passage 52 and inward of the fluid system. In such case, fluid within the system acts on said surface portion 62 to aid in closing passage 52, to in turn maintain the passage 52 in a closed state.

In addition, rubber member 46 defines on side 50 thereof an annular surface portion 64 which is also angled toward the passage 52 and inward of the fluid system. Such surface portion 64 aids in directing the probe 66 to the passage 54, so that it can be properly inserted therethrough. The aperture 68 in washer 60 may be sized and located to aid in proper positioning of the probe 66, as shown.

Shown in FIGS. 3 and 4 is a third embodiment of fitting 70. Such fitting 70 is adapted for use within an aperture 72 defined through a fluid carrying body 74, carrying system fluid. A resilient member 76 is disposed within the aperture 72, and has one side 78 thereof exposed to fluid within the system, and the other side 80 exposed to outside the system. The resilient member 76 defines a passage 81 from one side to the other side thereof, as shown.

An annular step 82 is defined by the fluid carrying body 74, and an adapter member 84 is threaded into a threaded portion of the aperture 72 as shown. The adapter member 84 defines an annular surface portion 86 which bears on the other side of the resilient member 76 about the edge thereof, the annular step 82 bearing on the one side of the resilient member 76 about the edge thereof. Through such means, the resilient member 76 is held within the aperture 72, in continuous substantially sealing relation with the fluid carrying body 74.

The fluid carrying body defines an annular surface 88 within aperture 72 which is angled downwardly inwardly of the aperture 72 toward the fluid within the system. Such annular surface 88 is in continuous annular contact with the resilient member 76, so as to compress the resilient member 76 to close the passage 81 and hold the passage 81 closed (FIG. 4).

In the use of such embodiment 70, the probe means 90 include a threaded portion 92 engageable with threads defined within a bore in the adapter member 84. The probe means 90 are then rotated until the tip 94 thereof extends through and opens passage 81, and into the fluid system. The probe means 90 are removed of course by rotation thereof in the opposite direction, allowing the passage 81 to close, whereby the system is maintained in a closed condition.

When the probe means 90 are not in use, a sealing plug 96 is applied as shown to protect and block off the resilient member 76.

It will be seen that all embodiments of fitting disclosed herein allow testing by means of a probe of a closed fluid system, meanwhile insuring that the system is maintained in such closed state, with no system shutdown required, and no loss of fluid therefrom. In addition, each fitting, it will be seen, is extremely simple in design and operation.

What is claimed is:

1. Apparatus for allowing introduction of a testing probe into a closed fluid system, meanwhile maintaining such system in its closed condition, comprising: a tubular member communicating with the fluid within the system; a resilient member disposed within the tubular member and having one side exposed to the fluid within the system and the other side exposed to outside the system, said resilient member defining a passage from said one side to said other side thereof; means for holding the resilient member within the tubular member in continuous substantially sealing relation therewith; means for compressing said resilient member to close said passage and hold said passage closed to maintain the system in a closed state; said probe means being introducible from the other side of the resilient member into and through said passage in sealing engagement with the resilient member, opening said passage thereby, and into the fluid system, the removal of the probe means allowing said passage to close, whereby the system is continuously maintained in a closed condition, wherein the means for holding the resilient member and tubular member in continuous substantially sealing relation therewith comprise a clamp member threadably associated with the tubular member and defining an annular surface positioned to bear on the resilient member on said other side thereof about the edge thereof, and an annular step defined by the tubular member and positioned to bear on the resilient member on said one side thereof about the edge thereof, wherein the means for compressing said resilient member to close said passage and hold said passage closed comprise said annular surface defined by the clamp member and said annular step portion defined by the tubular member, angled together outwardly of the resilient member and positioned about portions of the resilient member to compress the resilient member inwardly to close said passage and to hold said passage closed.

2. Apparatus according to claim 1 wherein the resilient member defines an annular surface portion on the one side thereof exposed to the fluid within the system and angled toward the passage defined thereby inwardly of the fluid system, whereby the fluid within the system acts on such resilient member annular surface portion to aid in closing such passage and maintaining said passage in a closed state.

3. Apparatus for allowing introduction of a testing probe into a closed fluid system including a fluid carrying body, meanwhile maintaining said fluid system in a closed condition, comprising: a resilient member disposed within an aperture defined through the fluid carrying body and having one side exposed to the fluid within the system and the other side exposed to outside the system, said resilient member defining a passage from said one side to said other side thereof; means for holding the resilient member within the aperture in continuous substantially sealing relation with the fluid carrying body; means for compressing said resilient member to close said passage and hold said passage closed to maintain the system in a closed state; said probe means being introducible from the other side of the resilient member into and through such passage in sealing engagement with the resilient member, opening said passage thereby, and into the fluid system, the removal of the probe means allowing said passage to close, whereby the system is continuously maintained in a closed condition, wherein the means for holding the resilient member within the aperture in continuous substantially sealing relation therewith comprise an adapter member threadably associated with the fluid carrying body and defining an annular surface portion to bear on the resilient member on the other side thereof about the edge thereof, and an annular step defined by the fluid carrying body and positioned to bear on the resilient member on the other side thereof about the edge thereof, wherein the means for compressing the resilient member to close said passage and hold said passage closed comprise an annular surface defined by the fluid carrying body within the aperture, angled downwardly inwardly of the aperture toward the fluid within the system, and in continuous annular contact with the resilient member.

* * * * *